United States Patent [19]
Nakano et al.

[11] Patent Number: 5,998,522
[45] Date of Patent: *Dec. 7, 1999

[54] COATING SOLUTION AND METHOD FOR PREPARING THE COATING SOLUTION, METHOD FOR FORMING INSULATING FILMS FOR SEMICONDUCTOR DEVICES, AND METHOD FOR EVALUATING THE COATING SOLUTION

[75] Inventors: Tadashi Nakano; Makoto Shimura; Tomohiro Ohta, all of Chiba, Japan

[73] Assignee: Kawasaki Steel Corporation, Hyogo, Japan

[ * ] Notice: This patent is subject to a terminal disclaimer.

[21] Appl. No.: 09/042,668

[22] Filed: Mar. 17, 1998

Related U.S. Application Data

[63] Continuation of application No. 08/545,736, filed as application No. PCT/JP94/01910, Nov. 11, 1994, Pat. No. 5,840,821.

[30] Foreign Application Priority Data

Mar. 11, 1994 [JP] Japan ...................................... 6-41314

[51] Int. Cl.$^6$ .................................................. C08K 5/10
[52] U.S. Cl. ........................... 524/315; 524/317; 524/366; 524/376; 528/10; 528/43
[58] Field of Search ........................ 528/10, 43; 524/376, 524/366, 315, 317

[56] References Cited

U.S. PATENT DOCUMENTS

| | | |
|---|---|---|
| 4,349,609 | 9/1982 | Takeda et al. . |
| 4,605,446 | 8/1986 | Isozaki . |
| 4,670,299 | 6/1987 | Fukuyama et al. . |
| 4,723,978 | 2/1988 | Clodgo et al. . |
| 4,798,629 | 1/1989 | Wood et al. . |
| 4,865,649 | 9/1989 | Kashiwagi et al. . |
| 5,043,789 | 8/1991 | Linde et al. . |
| 5,152,833 | 10/1992 | Allman . |
| 5,286,572 | 2/1994 | Clodgo et al. . |
| 5,401,821 | 3/1995 | Geck et al. . |
| 5,840,821 | 11/1998 | Nakano et al. ............................ 528/10 |

FOREIGN PATENT DOCUMENTS

| | | |
|---|---|---|
| 0021818 | 1/1981 | European Pat. Off. . |
| 0226208 | 6/1987 | European Pat. Off. . |
| 0424638 | 5/1991 | European Pat. Off. . |
| 0474383 | 3/1992 | European Pat. Off. . |
| 62-32357 | 2/1987 | Japan . |
| 62-8146 | 2/1987 | Japan . |
| 62-230828 | 10/1987 | Japan . |
| 4-40347 | 2/1992 | Japan . |
| 4-233732 | 8/1992 | Japan . |
| 4-263429 | 9/1992 | Japan . |
| 4-320337 | 11/1992 | Japan . |
| 5-70119 | 3/1993 | Japan . |
| 5-333553 | 12/1993 | Japan . |

OTHER PUBLICATIONS

Y. Namba et al., "Global Planarization by Using the Reflow Step of Ladder Silicone SOG," Proceedings of the 44$^{th}$ Symposium on Semiconductors and Integrated Circuits Technology, the Electrochemical Society of Japan, Electronic Materials Committee, Tokyo, Jun. 17–18, 1993.

Furusawa et al., "New Reflowable Organic Spin–On Glass for Advanced Gap–Filling and Planarization", Jun. 7–8, 1994, VMIC Conference, pp. 186–192.

Besland et al., "Silicon and Carbon Solid–State MAS and Liquid–State NMR Study of the Polycondensation of Heteropolysiloxanes", *Journal of the American Chemical Society*, vol. 113, pp. 1982–1987, 1991.

Somero et al., "An Integrated, Low Temperature Interlayer Dielectric Using ECR Technology for Advanced CMOS ASIC and Logic Applications", (1992), 1992 VMIC Conference, pp. 72–78..

Matsuo et al., "Low Temperature Chemical Vapor Deposition Method Utilizing an Electron Cyclotron Resonance Plasma", (1983), *Japanese Journal & Applied Physics*, pp. L210–L213.

Machida et al., "SiO$_2$ Planarization Technology with Biasing and Electron Cyclotron Resonance Plasma Deposition for Submicron Interconnections", (1986), J. Vac. Sci. Technol. B 4 (4), pp. B4, 818–821.

SOG Technology, Oyo Butsuri (Applied Physics), (1988) vol. 57, No. 12, pp. 1931–1932.

Merck Index, p. 440, 9$^{th}$ Ed. (1976).

Vines et al., "Interlevel Dielectric Planarization with Spin–On Glass Films", (1986), 1986 VMIC Conference, pp. 506–515.

Chebi et al., "A Manufacturable ILD Gap Fill Process With Biased ECR CVD", (1991), 1991 VMIC Conference, pp. 61–67.

Pelnar et al., Functional Group Identification by Two–Dimensional $^{29}$Si NMR Spectroscopy with Reversed Detection and Signal Winnowing, *Applied Technology*, vol. 44, No. 3, pp. 396–400, 1990.

*Primary Examiner*—Melvin I. Marquis
*Attorney, Agent, or Firm*—Oliff & Berridge, PLC

[57] ABSTRACT

A coating solution for forming an insulating film used in production of semiconductor devices includes siloxanes represented by a general formula:

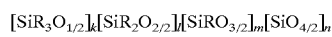

where each of k, l, m and n is an integer, R may be the same or different and represents at least one organic group, and a ratio of (3k+2l+m) to (k+l+m+n) is between about 0.8 and about 1.3. The present invention further relates to a method for preparing the coating solution, and a method for forming the insulating film using the coating solution, including the steps of coating the coating solution on a surface of a substrate of the semiconductor device to form a coated film, fluidizing the coated film at a temperature between about 150° C. to about 300° C. to planarize the surface of the substrate, and curing the fluidized coated film to form the insulating film. The present invention permits the formation of the insulating film with excellent properties such as an ability of fill up fine grooves and to planarize the surface of the substrate, and a small shrinkage factor. The method for evaluating the coating solution using $^{29}$Si-NMR technique is also described.

18 Claims, 4 Drawing Sheets

$$DOP (\%) = \{1-(\theta/90)(d_o/d_m)\} \times 100$$

COATING SOLUTION AND METHOD FOR PREPARING THE COATING SOLUTION, METHOD FOR FORMING INSULATING FILMS FOR SEMICONDUCTOR DEVICES, AND METHOD FOR EVALUATING THE COATING SOLUTION

This is a Continuation of application Ser. No. 08/545,736 filed Nov. 21, 1995, now U.S. Pat. No. 5,840,821 which is the U.S. National Stage of PCT/JP94/01910, filed Nov. 11, 1994. The entire disclosure of the prior application(s) is hereby incorporated by reference herein in its entirety.

TITLE OF THE INVENTION

Method for Evaluating Siloxanes Used for Forming Insulating Films, Coating Solution for Forming Insulating Films and Method for Preparing the Same, Method for Forming Insulating Films for Semiconductor Devices and Method for Producing Semiconductor Devices Using the Insulating Film-Forming Method.

TECHNICAL FIELD

The present invention relates to a method for evaluating siloxanes used for forming an insulating film which comprises determining the rates of structural units of siloxanes including, in particular, organic substituents directly bonded to Si atoms as a part of the structure thereof, present in a coating solution for forming an insulating film, i.e. a solution containing siloxanes which are used as precursors for forming an insulating film to level the surface of a substrate on which uneven portions are formed and to electrically insulate the substrate, in particular, an interlayer insulating film for leveling distributing wire structures of electronic devices such as an LSI multilevel interconnection structure and for insulating the multilevel interconnection structure, and evaluating the siloxanes on the basis of the rates thus determined; a coating solution for forming an insulating film, which comprises siloxanes and is used for producing a semiconductor device and a method for preparing the coating solution; and a method for forming an insulating film for semiconductor devices and a method for producing a semiconductor device using the insulating film-forming method.

BACKGROUND ART

Heretofore, the integration density of the semiconductor device has been increased, more finer and highly multilayered distributing wires for elements have correspondingly been required and, in turn, the steps formed between these distributing wires have increasingly been high. For this reason, the ability of an insulating material to fill up the gap formed between distributing wires and the surface flatness of an element after forming an insulating film have become serious problems. With regard to the tolerance in the flatness, the depth of focus of a resist becomes small for ensuring a desired resolution during the photolithography process and there has been reported that the unevenness of the surface of, for instance, a line-and-space pattern of 0.7 μm should be limited to the level of not less than 200 nm. A chip or wafer must satisfy the foregoing requirement throughout the entire area thereof and therefore, the complete leveling of the chip or wafer throughout the entire area thereof is required according to its literal sense.

To solve these problems, there has presently been known a method for filling up steps on the surface of a substrate to thus level the surface through the formation of an insulating film by the chemical vapor deposition method using ozon and tetraethoxysilane as starting materials ($O_3$-TEOS AP-CVD), as disclosed in Japanese Un-Examined Patent Publication (hereinafter referred to as "J. P. KOKAI") No. Sho 61-77695.

The $O_3$-TEOS APCVD technique is excellent in the step coverage and can ensure excellent filling up properties, but the insulating film is formed in conformity with distributing wires and therefore, it is impossible to level the surface of a substrate over a wide area thereof. Moreover, the $O_3$-TEOS APCVD technique also suffers from a problem such that the rate of deposition observed on a wide flat portion differs from that observed on fine and dense distributing wire patterns and accordingly, it is difficult to flatten the surface of a pattern whose distributing wire density varies depending on the position.

In addition, there has also been known a method which comprises grinding the surface of a thick deposited insulating film by the chemical mechanical polishing (CMP) technique as disclosed in, for instance, L. B. Vines and S. K. Gupta, 1986 IEEE VLSI Multilevel Interconnect Conference, p. 506, Santa Clara, Calif. (1986) or R. Chebi and S. Mittal, 1991 IEEE VLSI Multilevel Interconnect Conference, p. 61, Santa Clara, Calif. (1991) or B. M. Somero, R. P. Chebi, E. U. Travis, H. B. Haver, and W. K. Morrow, 1992 IEEE VLSI Multilevel Interconnect Conf., p. 72, Santa Clara, Calif. (1992). It has been said that the CMP technique permits almost ideal leveling of the surface over a wide area if appropriately establishing the conditions for the CMP technique.

However, grooves present between distributing wires should separately be filled up prior to carrying out CMP. More specifically, the CMP technique must be used in combination with other methods such as the CVD technique to fill up such grooves. Moreover, it has been pointed out that the CMP technique per se suffers from various problems to be solved such as a decrease in the throughput, formation of particles, metal/alkali contamination, uncertainty in the detection of the end point of polishing and an increase in the cost of equipment and accordingly, this technique has not yet been widely used.

If taking notice of only the techniques for filling up the grooves between distributing wires, the high density plasma CVD technique in which a substrate is biased (Biased HPD CVD) has attracted interest recently. S. Matsuo and M. Kiuchi, Jpn. J. Appl. Phys., 22, L210 (1983) or K. Machida and H. Oikawa, J. Vac. Sci. Technol., B4, 818 (1986). This technique is a method comprising depositing an oxide film while anisotropically sputter-etching the surface of a substrate with argon ions, unlike the currently used CVD technique, and the technique makes use of ECR or ICP which can ensure a high plasma ion density as a plasma source.

The HDP technique for forming interlayer insulating films is considered to be an almost satisfactory technique for filling up grooves, but projections are formed on the entire surface of a distributing wire pattern due to insufficient sputter etching and therefore, the leveling of the surface should separately be carried out by, for instance, the CMP technique. Moreover, the problems such as particle-formation and reduction in throughput due to the low deposition rate have not yet been solved.

On the other hand, there has widely been adopted, in the production of semiconductor devices, a method for relieving the unevenness of a substrate by forming an insulating film according to the SPIN ON GLASS (SOG) method as disclosed in, for instance, OYO BUTSURI (Applied Physics), Vol. 57, No. 12 (1988). For instance, a hard film comprising $SiO_2$ formed by the SOG method has generally been used as an interlayer insulating film for LSI multilevel interconnections.

The term "SOG" means a technique comprising applying a solution containing oligosilanols or oligosilicates to a substrate by a spincoater and then thermally hardening the coated solution to form a hard film of $SiO_2$, or an insulating film formed by the method, or a coating liquid for forming an insulating film. The SOG coating solution may run into narrow grooves formed between distributing wires and the film thus formed may correspondingly fill up the grooves and simultaneously flow into wide and flat recesses. Therefore, the coating solution also permits leveling of the surface having relatively wide and high steps. The SOG process is performed at a low temperature on the order of about 400° C. and therefore, it can be recomended to use the solution for forming interlayer insulating films after the formation of Al distributing wires which are apt to be easily damaged by heating.

There have conventionally been used, as materials for SOG, an oligosilicate called inorganic SOG represented by the general formula: $Si(OR)_n(OH)_{4-n}$ and completely free of organic groups bonded to Si atoms. The inorganic SOG undergoes volume shrinkage at a rate of about 20% during hardening with heating. Accordingly, the resulting film has a poor resistance to crack and the inorganic SOG can be coated in a thickness ranging from only 200 to 300 nm by a single coating operation. An SOG film having a thickness at least equal to the height of distributing wires is required for relieving the steps formed by distributing wires whose cross section has an aspect ratio greater than about 1, but such a thick SOG film cannot be formed because the inorganic SOG may cause cracking. In other words, the inorganic SOG cannot be used for leveling a stepped pattern having a high cross sectional aspect ratio.

To eliminate the foregoing drawbacks associated with the inorganic SOG and to improve the shrink properties, flatness, adhesion and resistance to cracks of a film as well as the etch rate thereof, there has been investigated and developed an oligosiloxane called organic SOG which comprises, in the chemical structure, organic substituents directly bonded to an Si atom, i.e., an organic Si and which is represented by the general formula: $R_m Si(OR)_n (OH)_{4-n-m}$. Methyl group is mainly used as the organic substituent because of its thermal stability, gas-generating properties, resistance to plasma, yield value of the resulting film and flexibility thereof, but other kinds of substituents such as a phenyl group may sometimes be used as the organic substituent. The organic SOG is characterized in that the film thereof has a low shrinkage factor during hardening with heating as compared with the film of the inorganic SOG and therefore, the film has high resistance to cracks. In addition, the rate of etching the film with a $CHF_3$-containing etching gas is low and almost comparable to that of the CVD film. Therefore, the organic SOG permits the use of a leveling process by the equal velocity etch back method which comprises applying a thick organic SOG layer on a CVD oxide film formed on a pattern, then hardening the organic SOG layer and etching the hardened SOG layer with a $CHF_3$-containing etching gas simultaneously with the CVD film.

However, the hardening of the SOG layer by heating is initiated at about 100° C. and this is accompanied by the volume shrinkage of the SOG layer. Thus, the surface which is once flatened by the application of the organic SOG ultimately has unevenness corresponding to the shape of the surface of a substrate and the flatness of the surface is not improved so much.

Moreover, it has been believed that the range of the area on a substrate which is under the influence of the leveling effect due to the flow of the coating solution is limited to local one and only on the order of 10 μm and thus the thickness of the film on the recesses between wide distributing wires of not less than 10 μm is approximately identical to that of the film on the projected portions, i.e., on the distributing wires. More specifically, the steps formed between resesses and projected portions are not relieved at all from the visual field on the order of not less than 10 μm. As has been discussed above, the thickness of the film formed varies depending on the density of the wiring pattern and therefore, the organic SOG is useless for leveling a wide area comparable to those of chips and wafers.

Moreover, the organic SOG undergoes volume shrinkage on the order of at least about 7% during hardening with heating and may crack due to the contraction stress if a film thereof having a thickness of not less than 500 nm is formed by coating, like the inorganic SOG.

The organic SOG film is inferior in the quality and liable to retain or absorb water. For this reason, various troubles are liable to arise due to the gas generated from the SOG film in the subsequent processes. Moreover, the organic SOG film suffers from various problems such that the apparent dielectric constant thereof increases due to the presence of water, the delay increases due to the interline capacity and thus it is insufficient for use as an insulating film for high speed interconnections.

There has been reported several kinds of SOG's which can eliminate the foregoing drawbacks associated with the organic SOG. One of them is a ladder siloxane oligomer which can be represented by the following structural formula:

In other words, a methyl group (or a phenyl group) is bonded to each Si atom and the oligomer has a ladder-like regular structure.

The ladder siloxane oligomer causes melt flow through heating like the crystals because of high structural regularity, but suffers from fatal drawbacks such that it cannot form a thick film because of the high shrinkage factor and poor resistance to cracks and that it is lacking in structurally active hydroxyl groups (Si—OH), poorly adhered to the substrate and is liable to cause peeling.

As another measure, there has been known an inorganic SOG prepared from hydrogensiloxane oligomer or perhydrosilazane oligomer. These novel SOG's have a structure free of organic groups directly bonded to Si atoms and are, instead, characterized by having hydrogen atoms directly bonded to Si atoms. Either of them can be used for forming a thick film since it undergoes expansion through absorption of oxygen present in the atmosphere in a furnace during hardening with heating after coating and drying and accordingly has a low apparent shrinkage factor. However, they suffer from a problem such that the uneven shape of the substrate surface is traced on the films thereof due to the shrinkage during application and drying thereof, like the organic SOG and therefore, they cannot be used for leveling the surface over a wide area. Furthermore, free hydroxyl groups remain in the film even after hardening with heating and this becomes a cause of gas-generation and a high dielectric constant.

There has not yet been developed any material which can solve the problems listed above.

On the other hand, the improvement of characteristic properties of insulating films for semiconductor devices, in particular, interlayer insulating films for the LSI multilevel interconnection requires the analysis of the siloxanes constituting the insulating films.

As methods for analyzing siloxanes included in a variety of materials, there have been known those comprising analyzing a sample as such or siloxanes extracted with an appropriate organic solvent by, for instance, infrared spectrophotometry, nuclear magnetic resonance (NMR) spectroscopy, inductive coupled plasma emission spectroscopic analysis (J. P. KOKAI No. Hei 4-40347). In addition, there has also been known a method which comprises chemically decomposing siloxanes to form decomposition products thereof and detecting and analyzing the products (Japanese Examined Patent Publication (hereinafter referred to as "J. P. KOKOKU") No. Sho 62-8146). However, the purpose of all of these methods is to determine the total amount of Si present in a specific material.

Although several methods for analyzing siloxanes have been known as has been discussed above, there has not yet been established any industrially effective method for determining the proportions of organic substituents present in the organic SOG and, in particular, any industrially useful method for accurately and simply analyzing and evaluating the organic SOG, i.e., siloxanes for forming insulating films while correlating the results with the characteristic properties of insulating films for semiconductor devices, in particular, interlayer insulating films for the LSI multilevel interconnection. Moreover, there have been desired for the development of a coating solution for forming an insulating film which can sufficiently improve the characteristic properties of insulating films for semiconductor devices, in particular, interlayer insulating films for the LSI multilevel interconnection and a method for preparing the same as well as a method for forming an insulating film for semiconductor devices.

DISCLOSURE OF THE INVENTION

The present invention has been developed for the solution of the foregoing problems associated with the conventional techniques and accordingly, an object of the present invention is to provide a method comprising analyzing the rates of organic substituents present in an organic SOG, and determining the rates of Si atoms bonded to different numbers of organic groups, i.e., structural units present in the organic SOG or siloxanes for forming an insulating film for semiconductor devices; and evaluating the siloxanes for forming insulating films on the basis of the results obtained through the analysis, for the purpose of forming an insulating film, in particular, an interlayer insulating film having excellent film characteristic properties.

Another object of the present invention is to provide a coating solution for forming an insulating film using siloxanes, which permits completely filling up fine grooves, formation of a film having a thickness sufficient for eliminating steps on the substrate surface and uniform (and global) leveling of the entire pattern formed on the substrate and which permits the formation of an insulating film free of water, having a low dielectric constant and favorable for a high speed interconnection, i.e., an insulating film excellent in film characteristic properties, in particular, an interlayer insulating film for semiconductor devices, as well as a method for preparing the coating solution, a method for forming an insulating film for semiconductor devices and a method for producing a semiconductor device using the insulating film-forming method.

The inventors of this invention have conducted intensive studies on characteristic properties of siloxanes and interlayer insulating films for LSI multilevel interconnections obtained using siloxanes, have found out that the characteristic properties of the insulating film are greatly influenced by the rates of organic substituents present in the siloxanes or the rates of Si atoms carrying different numbers of organic groups bonded thereto, i.e., the rates of structural units of the siloxanes present in the organic SOG and that, as a result of intensive studies, the organicity of SOG can be evaluated on the basis of the integrated values of $^{29}$Si-NMR spectral signals and that an insulating film having excellent film characteristic properties can be obtained by the use of a coating solution of an organic SOG prepared while taking into consideration the results of the foregoing evaluation, and thus have completed the present invention.

According to a first embodiment of the present invention, there is provided a method for evaluating siloxanes for forming an insulating film which comprises evaluating siloxanes which comprise Si atoms each carrying at least one organic substituent bonded thereto contained in a coating solution for forming an insulating film, characterized by determining the rates of three kinds of Si atoms each having the number of the organic substituents bonded thereto ranging from 1 to 3 and the rate of at least one of Si atoms free of the foregoing organic substituent to thus determine, for instance, the content of organic substituents on the basis of the foregoing proportions and evaluating the siloxanes for forming an insulating film, for instance, the organicity thereof.

In this respect, the rates of the Si atoms carrying different numbers of organic substituents bonded thereto are preferably determined through the use of the integrated values of $^{29}$Si-NMR spectral signals.

In addition, it is preferred that the siloxanes which comprise the Si atoms each carrying at least one organic substituent bonded thereto be those for forming an interlayer insulating film for LSI multilevel interconnections represented by the following Formula [1] and that the proportion of at least one of the following structural units (a), (b), (c) and (d) present in the siloxanes be determined by the integrated values of $^{29}$Si-NMR spectral signals.

In Formula [1a], or equivalently $$[SiR_3O_{1/2}]_k[SiR_2O_{2/2}]_l[SiRO_{3/2}]_m[SiO_{4/2}]_n \quad [1b]$$

k, l, m and n each represents an integer ranging from 0 to 1000, and at least one of k, l and m is greater than zero; R may be the same or different and represents at least one organic group selected from the group consisting of saturated hydrocarbon groups, unsaturated hydrocarbon groups, and a phenyl group, provided that the phenyl group may be a substituted phenyl group; and the oxygen atoms each is linked to either of Si, R and H.

In the foregoing structural units (a), (b), (c) and (d), R may be the same or different and represents at least one organic group selected from the group consisting of saturated hydrocarbon groups, unsaturated hydrocarbon groups and phenyl group, provided that the phenyl group may be a substituted phenyl group.

Moreover, the siloxanes comprising the Si atoms carrying at least one kind of the organic group are preferably siloxane oligomers. The degree of polymerization of the siloxane oligomer represented by the number of the repeating structural units [k+l+m+n] preferably ranges from 2 to 500.

According to a second embodiment of the present invention, there is provided a coating solution for forming an insulating film, which is a coating solution for forming an insulating film used in the production of semiconductor devices, wherein the solution comprises siloxanes which comprise Si atoms carrying at least one kind of organic substituent bonded thereto, which are represented by the following general formula [1a] and whose rate, X, represented by the following Formula [2] and determined by the integrated values of $^{29}$Si-NMR spectral signals, satisfies the relation defined by Formula [2]:

In Formula [1a], or equivalently

$$[SiR_3O_{1/2}]_k[SiR_2O_{2/2}]_l[SiRO_{3/2}]_m[SiO_{4/2}]_n, \quad [1b]$$

k, l, m and n each represents an integer ranging from 0 to 1000, and at least one of k, l and m is greater than zero; R may be the same or different and represents at least one organic group selected from the group consisting of saturated hydrocarbon groups, unsaturated hydrocarbon groups, and a phenyl group, provided that the phenyl group may be a substituted phenyl group; and the oxygen atoms each is linked to either of Si, R and H;

$$X = \frac{A_1}{A_0 + A_1 + A_2 + A_3} \times 100 \geq 80\% \quad [2]$$

In Formula [2], $A_0$ is the area of the Si signal ascribed to Si atoms free of Si—C bond and determined by the $^{29}$Si-NMR spectral analysis; $A_1$ is the area of the Si signal ascribed to Si atoms each having a single Si—C bond and determined by the $^{29}$Si-NMR spectral analysis; $A_2$ is the area of the Si signal ascribed to Si atoms each having two Si—C bonds and determined by the $^{29}$Si-NMR spectral analysis; and $A_3$ is the area of the Si signal ascribed to Si atoms each having three Si—C bonds and determined by the $^{29}$Si-NMR spectral analysis.

Moreover, the Si atom free of any Si—C bond, the Si atom having a single Si—C bond, the Si atom having two Si—C bonds and the Si atom having three Si—C bonds are preferably Si atoms included in the following structural units (c), (a), (b) and (d) respectively:

(a)

(b)

In the foregoing structural units (a), (b), (c) and (d), the substituent R may be the same or different and represents at least one organic group selected from the group consisting of saturated hydrocarbon groups, unsaturated hydrocarbon groups and phenyl group, provided that the phenyl group may be a substituted phenyl group.

Moreover, the foregoing siloxanes are preferably siloxane oligomers. The degree of polymerization of the siloxane oligomer represented by the number of the repeating structural units: [k+l+m+n] preferably ranges from 2 to 500.

Moreover, the present invention provides the foregoing coating solution for forming an insulating film wherein the foregoing siloxanes are dissolved in a solvent mainly comprising an organic compound having a boiling point of not less than 120° C. and not more than 200° C.

According to a third embodiment of the present invention, there is provided a coating solution for forming an insulating film used in the production of semiconductor devices, wherein a methylsiloxane oligomer represented by the chemical formula: $(CH_3)_y \, SiO_{2-(y/2)}$ (in the formula, y is not less than 0.8 and not more than 1.3) and having a weight-average molecular weight of not less than 1500 and not more than 6000 and a random structure is dissolved in a solvent mainly comprising an organic compound having a boiling point of not less than 120° C. and not more than 200° C.

In this regard, the solvent preferably has a coefficient of viscosity, as determined at 25° C., of not more than 2.0 cP and preferably comprises at least one member selected from the group consisting of ethylene glycol monoethyl ether, ethylene glycol monoisopropyl ether, propylene glycol monomethyl ether, ethylene glycol monoethyl ether acetate, diethylene glycol dimethyl ether, di-n-butyl ether, di-isobutyl ether, di-n-amyl ether, methyl n-amyl ketone, methyl isoamyl ketone, n-amyl acetate, isoamyl acetate and n-hexyl acetate.

According to a fourth embodiment of the present invention, there is provided a method for preparing a coating solution for forming an insulating film which makes use of a compound selected from the group consisting of tetraalkoxysilanes, methyltrialkoxysilanes and dimethyldialkoxysilanes or mixtures of at least two of them as a starting material, and which comprises the steps of blending the starting materials in such a manner that the molar concentration of Si—CH₃ in the resulting blend is not less than 80% and not more than 130% on the basis of the molar concentration of Si present in the total starting materials, adding water to the blend in an amount of 2 to 4 times the molar amount of the blend, heating the mixture at a temperature of not less than 30° C. and not more than 80° C. in the presence of an organic carboxylic acid as a catalyst to thus polymerize the mixture, diluting the polymerized product by addition of a solvent mainly comprising an organic compound having a boiling point of not less than 120° C. and not more than 200° C. and then distilling the diluted solution under ordinary pressure or a reduced pressure to thus distill off the water and the alcohol as by-products of the polymerization reaction.

In this method, the tetraalkoxysilane is preferably tetramethoxysilane and/or tetraethoxysilane; the methyltrialkoxysilane is preferably methyltrimethoxysilane and/or methyltriethoxysilane and the dimethyldialkoxysilane is preferably dimethyldimethoxysilane and/or dimethyldiethoxysilane. Preferably, the foregoing organic carboxylic acid is at least one member selected from the group consisting of formic acid, acetic acid and succinic acid and the concentration thereof ranges from 1/1000 to 1/100 mole on the basis of the foregoing starting material.

In the foregoing method for preparing a coating solution for forming an insulating film, an alcoholic solvent is preferably added to the polymerization system in an amount ranging from 0.2 to 3 times the molar amount of the starting material prior to the polymerization reaction, and the alcoholic solvent is preferably at least one member selected from the group consisting of methanol, ethanol and dioxane.

Moreover, the foregoing solvent preferably has a coefficient of viscosity, as determined at 25° C., of not more than 2.0 cP and the solvent is preferably at least one member selected from the group consisting of ethylene glycol monoethyl ether, ethylene glycol monoisopropyl ether, propylene glycol monomethyl ether, ethylene glycol monoethyl ether acetate, diethylene glycol dimethyl ether, di-n-butyl ether, di-isobutyl ether, di-n-amyl ether, methyl n-amyl ketone, methyl isoamyl ketone, n-amyl acetate, isoamyl acetate and n-hexyl acetate.

According to a fifth embodiment of the present invention, there is provided a method for forming an insulating film for semiconductor devices which comprises the steps of applying the foregoing coating solution for forming an interlayer insulating film onto a distributing wire pattern formed on a silicon substrate and having step-like unevenness on the surface of the pattern, then drying the coated solution, maintaining the dried coating solution at a temperature of not less than 150° C. and not more than 300° C. for not less than 30 seconds to thus fluidize it and then hardening it at a temperature of not less than 350° C. and not more than 450° C. in a nitrogen gas atmosphere to form an insulating film.

Further the present invention also provides a method for producing a semiconductor device which makes use of the foregoing method for forming an insulating film for semiconductor devices.

BEST MODE FOR CARRYING OUT THE INVENTION

The present invention will hereinafter be described in more detail.

The first embodiment of the present invention relates to an evaluation method which comprises the steps of determining the rate of at least one Si atom carrying a different number of organic substituents bonded thereto, present in siloxanes which comprise Si atoms each carrying at least one kind of organic substituent bonded thereto and which are included in an insulating film-forming coating solution used for forming an insulating film for semiconductor devices such as an interlayer insulating film for LSI multilevel interconnections; determining, for instance, the contents of the organic substituents present in the siloxanes according to or on the basis of the rate of at least one Si atom determined above; and then evaluating the siloxanes, for instance, the organicity thereof on the basis of the contents of the organic substituents in the siloxanes. More specifically, the method comprises determining the rate and the contents on the basis of the areas of signals obtained by the $^{29}$Si-NMR spectroscopy and evaluating the organicity of the siloxanes.

The solution containing the siloxanes used in the present invention, i.e., the coating solution for forming an insulating film (hereinafter simply referred to as "coating solution") may be any solution containing siloxanes which is used as a precursor for forming an insulating film for semiconductors (hereinafter simply referred to as "insulating film") and which comprises siloxanes containing Si atoms each carrying at least one kind of organic substituent or any solution in which such siloxanes are dissolved in an organic solvent and examples thereof include SOG solutions for forming SOG films and organic SOG solutions. In this respect, the organic substituent may be at least one member selected from the group consisting of saturated hydrocarbon groups, unsaturated hydrocarbon groups and phenyl groups. Moreover, the number of organic groups bonded to one Si atom may range from 1 to 3.

The siloxanes usable in the present invention can be represented by the following Formula [1a], but the way how to link these structural units is not restricted to any specific one and they may be bonded in either linear or branched form. Moreover, they may be used in any combination.

[1a]

In Formula [1a], or equivalently $$[SiR_3O_{1/2}]_k[SiR_2O_{2/2}]_l[SiRO_{3/2}]_m[SiO_{4/2}]_n, \quad [1b]$$

k, l, m and n each represents an integer ranging from 0 to 1000, at least one of k, l, and m is greater than zero; R may be the same or different and represents at least one organic group selected from the group consisting of saturated hydrocarbon groups, unsaturated hydrocarbon groups, and phenyl groups, provided that the phenyl group may be a substituted phenyl group; and the oxygen atoms each is linked to either of Si, R and H.

Such siloxanes are preferably siloxane oligomers used for forming insulating films and more preferably siloxane oligomers each having a degree of polymerization ranging from 2 to 500. More specifically, the number of the following repeating structural units (a) to (d): [k+l+m+n] of the siloxane oligomer represented by the foregoing Formula [1] preferably ranges from 2 to 500. In this regard, if the degree of polymerization (number of repeating units) exceeds 500, the viscosity of a coating solution (SOG solution) comprising siloxane and a solvent becomes extremely high, while if it is less than 2, the siloxane is easily evaporated during the insulating film-forming step and in any case, it is difficult to form an insulating film.

In the foregoing structural units (a), (b), (c) and (d), the substituent R may be the same or different and represents at least one organic group selected from the group consisting of saturated hydrocarbon groups, unsaturated hydrocarbon groups and phenyl group, provided that the phenyl group may be a substituted phenyl group.

When evaluating siloxanes for forming insulating films, the method of the present invention comprises the step of determining the contents of organic substituents of the siloxanes; or analyzing Si atoms carrying different numbers of organic groups bonded thereto (Si atoms each having a number of Si—C bond ranging from 0 to 4), i.e., at least one of the foregoing structural units (a) to (d) to determine the rate thereof present in the siloxanes. The methods for determining the contents of organic substituents of siloxanes or for determining the rate of the foregoing structural units (a) to (d) present therein is not restricted to any specific one, but the nuclear magnetic resonance (NMR) spectroscopy technique is preferably used. More preferably, such rates of organic substituents are preferably obtained from the integrated values of $^{29}$Si-NMR spectral signals.

When carrying out the nuclear magnetic resonance (NMR) spectroscopic method, siloxanes such as SOG solution as a sample is first dissolved in a deutero solvent. The deutero solvent herein used is not restricted to any specific one insofar as it does not cause any separation of components of the SOG solution from the same through the addition of the solvent and examples thereof usable herein include deutero chloroform, deutero acetone and deutero methanol. If the concentration of the sample is too low, sufficient detection sensitivity is not expected, while if it is too high, the proportion of the deutero solvent is reduced and the frequency stability of the NMR spectrometer is impaired. Therefore, the concentration of the sample preferably ranges from 10 to 90%.

It is preferred to use a sample tube of Teflon in the $^{29}$Si-NMR measurement. This is because if using the usual glass sample tube for NMR measurement, signals ascribed to $^{29}$Si originated from the silicate glass appear in the NMR spectrogram.

In the $^{29}$Si-NMR measurement performed in the present invention, it is desirable that the decoupling of proton be not performed. This is because the nuclear Overhauser effect in the $^{29}$Si-NMR measurement is negative and correspondingly, the intensity of $^{29}$Si-NMR signals may sometimes be attenuated depending on samples. Thus, the quantitativeness of the intensity of the signal integration can be ensured.

Moreover, the addition of a relaxation agent such as tris(acetylacetonato)chromium (III) or tris(acetylacetonato) iron (III) is also preferred to reduce the measuring time.

Every signals in the $^{29}$Si-NMR spectrogram thus determined are identified and the rates of the structural units (a), (b), (c) and (d) or/and the contents of Si atoms carrying organic groups bonded thereto are determined on the basis of the signal areas thus obtained. The contents of organic groups can be defined in several different ways depending on the purposes and such different definitions may properly be used depending on the purposes or according to need. For instance, if the area of the Si signal ascribed to Si atoms free of Si—C bonds is denoted by $A_0$, the area of the Si signal ascribed to Si atoms each having a single Si—C bond is denoted by $A_1$, the area of the Si signal ascribed to Si atoms each having two Si—C bonds is denoted by $A_2$ and the area of the Si signal ascribed to Si atoms each having three Si—C bonds is denoted by $A_3$, the measure (represented by X) of the organicity of siloxanes can be defined by, for instance, the following Formula [3] or [4]:

$$X = \frac{A_1 + 2A_2 + 3A_3}{A_0 + A_1 + A_2 + A_3} \times 100 \quad [3]$$

$$X = \frac{A_1 + A_2 + A_3}{A_0 + A_1 + A_2 + A_3} \times 100 \quad [4]$$

Formula [3] is an equation representing the ratio of the number of organic substituents to the number of Si atoms present in the siloxane and Formula [4] is an equation representing the ratio of the number of organic Si atoms to the number of Si atoms present in the siloxane. The equation for evaluating the organicity is not restricted to the foregoing Formulas [3] and [4] and can be represented by other definitions depending on the purposes of the analysis.

In addition, the 2nd to 5th embodiments of the present invention relate to novel coating solutions containing siloxanes, which are evaluated according to the foregoing evaluation method, for forming an insulating film for semiconductor devices such as an interlayer insulating film for LSI multilevel interconnections (hereinafter simply referred to as "insulating film") and methods for forming insulating films using the coating solutions. The coating solution according to the 2nd embodiment and the method for forming an insulating film using the same will hereinafter be detailed.

The inventors have found out that there is a close relation between the chemical structure of siloxanes and the characteristic properties of the resulting SOG film.

More specifically, the inventors have found out that if using a coating solution containing siloxanes, preferably siloxane oligomers whose proportion X represented by the following relation and determined on the basis of the integrated values of $^{29}$Si-NMR spectral signals satisfies the following equation [2], the resulting insulating film exhibits excellent characteristic properties:

$$X = \frac{A_1}{A_0 + A_1 + A_2 + A_3} \times 100 \geq 80\% \quad [2]$$

In the foregoing Formula [2], $A_0$ is the area of the Si signal ascribed to Si atoms free of Si—C bond and determined by the $^{29}$Si-NMR spectral analysis; $A_1$ is the area of the Si signal ascribed to Si atoms each having a single Si—C bond and determined by the $^{29}$Si-NMR spectral analysis; $A_2$ is the area of the Si signal ascribed to Si atoms each having two Si—C bonds and determined by the $^{29}$Si-NMR spectral analysis; and $A_3$ is the area of the Si signal ascribed to Si atoms each having three Si—C bonds and determined by the $^{29}$Si-NMR spectral analysis.

The reason why an insulating film having excellent characteristic properties is formed when using a coating solution containing siloxanes whose proportion X defined by the foregoing Formula [2] is not less than 80% is, for instance, as follows: (1) the water absorption of the resulting film is reduced and therefore, the amount of generated gases and the dielectric constant thereof are restricted to low levels; (2) the resistance to cracks of the film is improved and accordingly, the coating solution can be applied in the form of a thick layer; and (3) the dry etch rate is reduced and therefore, a wide etch back margin can be ensured.

Then the coating solution for forming an insulating film according to the third embodiment of the present invention will be explained below.

In the coating solution according to this embodiment, the measure for the organicity of the siloxanes is evaluated on the basis of the foregoing Formula [3].

According to the third embodiment of the present invention, there is provided a coating solution characterized by dissolving a methylsiloxane oligomer represented by the chemical formula: $(CH_3)_y SiO_{2(y/2)}$ (in the formula, y is not less than 0.8 and not more than 1.3) and having a weight-average molecular weight of not less than 1500 and not more than 6000 and a random structure in a solvent mainly comprising an organic compound having a boiling point of not less than 120° C. and not more than 200° C. The coating solution is characterized in that the value y in the chemical formula is not less than 0.8 and not more than 1.3 unlike the conventional organic SOG (wherein y ranges from 0.3 to 0.6) and that the siloxane oligomer has a random structure while the conventional organic SOG includes a ladder siloxane having a regular structure.

The shrinkage of the methylsiloxane oligomer during hardening by heat-polymerization can be almost completely eliminated by limiting the value y in the chemical formula of the methylsiloxane oligomer to not less than 0.8. Therefore, the coating solution can be applied as a thick layer and is advantageous for leveling the layer. The water absorption of the methylsiloxane oligomer can be made almost zero and the dielectric constant thereof can be reduced to not more than 3.5, by the foregoing limitation. While if the value y is less than 0.8, the resulting film exhibits characteristic properties similar to those observed for the usual organic SOG and accordingly, the insulating films obtained are those simply having the shrinkage factor, water absorption, ability of flattening and dielectric constant thereof falling within the ranges achieved by the conventional techniques. On the other hand, if the value y exceeds 1.3, the heat-polymerization of the oligomer becomes difficult and does not form any film, but results in the formation of a rubbery substance. For this reason, the upper limit of y is defined to be 1.3.

According to the conventional techniques, it has been believed that the higher the value y, the lower the adhesion of the resulting film to the surface of a substrate and that such siloxane oligomer cannot practically be used. The ladder methylsiloxane is expressed by the chemical formula identical to that of the siloxane oligomer used in the present invention and the value y falls within the range defined in the present invention (the value y should be 1 to form a ladder structure), but it likewise suffers from problems of poor adhesion and high shrinkage and therefore, it is difficult to put it into practical use, as has already been discussed above in connection with the "Background Art".

In the present invention, the problem of reduction in the adhesion due to the use of the siloxane oligomer having a large y is solved by using siloxane oligomers comprising skeletons having random structures, limiting the molecular weight thereof and limiting the solvent to specific ones. Thus, it would be believed that the selection of such a random structure permits the incorporation of a large amount of Si—OH terminals which contribute to the adhesion into the oligomer structure, the resulting Si—O—Si network structure becomes sparse, whereby the film is softened and the ability of the film to absorb stresses is enhanced and accordingly, the adhesion of the resulting film is improved. Although there has not yet been developed any appropriate parameter for defining the random structure, the conventional organic SOG is liable to have a regular structure even if the value y is increased and accordingly, it is insufficient in the adhesion. If the molecular weight of the siloxane oligomer is less than 1500, it also undergoes a severe volume shrinkage during polymerization, an internal stress is easily generated and this becomes a cause of the formation of cracks and peeling. Furthermore, if using a solvent having a boiling point of less than 120° C., a problem of uneven coating arises due to the difference in drying rate between portions on a plane and stresses are generated severely and this has a bad influence upon the adhesion.

In the present invention, the weight-average molecular weight of the methylsiloxane oligomer is limited to the range of from 1500 to 6000 for the purpose of solving the foregoing problem of adhesion. Moreover, if the molecular weight is less than 1500, any continuous coating film cannot be formed, while if it exceeds 6000, the viscosity of the resulting coating solution becomes too high and this becomes a cause of the generation of radial unevenness called striation. The weight-average molecular weight of the siloxane oligomer most preferably ranges from 1500 to 3500.

A solvent mainly comprising an organic solvent having a boiling point of not less than 120° C. and not more than 200° C. is used as the solvent for dissolving the foregoing methylsiloxane oligomer. If the boiling point of the solvent is less than 120° C., most of the solvent is evaporated due to the rotational motion during the coating operation and therefore, the surface cannot be sufficiently flattened due to the filling up effect of the coating solution. Moreover, a problem of reduction in the adhesion arises due to the generation of stresses during drying operations as has been described above. On the other hand, if the boiling point of the solvent exceeds 200° C., the drying rate is considerably reduced. This leads to a decrease in the throughput, formation of defects during transportation of the substrates and problems of foaming and residual carbon during heating steps arise. Therefore, such a solvent cannot be used in the present invention. The boiling point of more preferably used solvents ranges from 130 to 160° C.

Incidentally, the coefficient of viscosity of the solvent greatly affects the ability of the coating solution to fill up fine grooves and the uniformity of the coated film. Therefore, the solvent used preferably has a coefficient of viscosity, as determined at 25° C., of not more than 2.0 cP. More specifically, if the coefficient of viscosity of the solvent is higher than 2.0 cP, the coating solution insufficiently runs into grooves of not more than 0.2 μm and there is observed, during application of the coating solution, a considerable increase in the frequency of the occurrence of so-called striation, i.e., unevenness in the film thickness in the form of radial striped pattern which extends from the center of a substrate towards the periphery thereof.

Examples of solvents which can satisfy the requirements of the present invention and accordingly can be used in the invention are ethylene glycol monoethyl ether, ethylene glycol monoisopropyl ether, propylene glycol monomethyl ether, ethylene glycol monoethyl ether acetate, diethylene glycol dimethyl ether, di-n-butyl ether, di-isobutyl ether, di-n-amyl ether, methyl n-amyl ketone, methyl isoamyl ketone, n-amyl acetate, isoamyl acetate and n-hexyl acetate.

These solvents may be used alone, but may also be used in any combination of at least two of them. Moreover, it is also possible to add, to the solvent, other low boiling point solvents such as methanol, ethanol, isopropyl alcohol, acetone, methyl ethyl ketone, water and butyl acetate in order to reduce the coefficient of viscosity and the coating properties of the resulting coating solution. In this regard, however, if adding a solvent other than those having a boiling point of not less than 120° C. and not more than 200° C., it is preferred that the volumetric rate thereof does not exceed 50% of the total volume of the solvent mixture. Incidentally, the foregoing solvents may of course be used for dissolving the siloxanes to prepare the coating solution according to the second embodiment of the present invention.

If using the coating solution satisfying the foregoing requirements, there is observed a quite characteristic phenomenon which can be called "self-fluidization", i.e., the film once dried and solidified is softened during heating, is again fluidized and the surface thereof is further flattened. The surface leveling due to the self-fluidization takes place at a temperature ranging from 150 to 200° C., which is lower than the temperature at which the methylsiloxane oligomer is condensed and hardened. This phenomenon permits the leveling of a considerably wider area as compared with the conventional SOG.

The use of either or both of the coating solutions according to the second and third embodiments of the present invention permits the achievement of uniform flatness over the entire pattern on the substrate surface, complete filling up of fine grooves, the formation of a thick film sufficient for leveling the steps formed on the substrate surface and the formation of an insulating film which is free of water, has a low dielectric constant, is excellent in the insulating properties and is suitably used for producing a high speed interconnection, for the reasons discussed above.

The organic SOG coating solution having such characteristic properties can be prepared by the method for preparing a coating solution according to the fourth embodiment of the present invention. More specifically, the method makes use of a compound selected from the group consisting of compounds such as alkoxysilanes and alkylalkoxysilanes, in particular, tetraalkoxysilanes, methyltrialkoxysilanes and dimethyldialkoxysilanes or a mixture of at least two of them as a starting material and the method comprises the steps of blending the starting materials in such a manner that the molar concentration of Si—$CH_3$ in the resulting blend is not less than 80% and not more than 130% on the basis of the molar concentration of Si present in the total starting materials, adding water to the blend in an amount of 2 to 4 times the molar amount of the blend, heating the mixture at a temperature of not less than 40° C. and not more than 80° C. in the presence of an organic carboxylic acid as a catalyst to thus polymerize the mixture, diluting the polymerized product by addition of a solvent mainly comprising an organic compound having a boiling point of not less than 120° C. and not more than 200° C. and then distilling the diluted solution under ordinary pressure or a reduced pressure to thus distill off the water and alcohol as by-products of the polymerization reaction.

In this method, the tetraalkoxysilane generally used is tetramethoxysilane ($Si(OCH_3)_4$) or tetraethoxysilane ($Si(OC_2H_5)_4$); the methyltrialkoxysilane generally used is methyltrimethoxysilane ($CH_3Si(OCH_3)_3$) or methyltriethoxysilane ($CH_3Si(OC_2H_5)_3$); and the dimethyldialkoxysilane is dimethyldimethoxysilane (($CH_3)_2Si(OCH_3)_2$) or dimethyldiethoxysilane (($CH_3)_2Si(OC_2H_5)_2$). At least one of these starting materials is blended in advance in such a manner that the molar concentration of Si—$CH_3$ in the resulting blend is not less than 80% and not more than 130% on the basis of the molar concentration of Si present in the total starting materials. The range of the concentration is equal to the range of the value y when methylsiloxane oligomer is expressed by the chemical formula: $(CH_3)_y SiO_{2(y/2)}$. In other words, the value y in the chemical formula should be limited to not less than 0.8 and not more than 1.3.

If methyltrimethoxysilane is, for instance, used as a starting material, the value, Si—$CH_3$/total Si, of the silane per se is 100% which corresponds to y=1 and therefore, methyltrimethoxysilane can be used alone. Moreover, if tetramethoxysilane and methyltrimethoxy-silane are mixed, the value y falling within the range: $0.8 \leq y < 1.0$ can be achieved by adjusting the mixing ratio r defined by [$Si(OCH_3)_4$]/[$CH_3Si(OCH_3)_3$] such that it falls within the range: $0 < r \leq 0.25$. If tetramethoxysilane and dimethyldimethoxysilane are mixed, the value y falling within the range: $0.8 \leq y \leq 1.3$ can be achieved by adjusting the mixing ratio r defined by [$Si(OCH_3)_4$]/[($CH_3)_2Si(OCH_3)_2$] such that it falls within the range: $7/13 \leq r \leq 1.5$. As has been discussed above, two or three kinds of starting materials may be used in combination.

If the molar concentration of Si—$CH_3$ included in the blend of starting materials or a single starting material is less than 80% of the molar concentration of Si included in the whole starting material, the value y of the resulting methylsiloxane oligomer, when the latter is represented by the chemical formula: $(CH_3)_y SiO_{2(y/2)}$, is less than 0.8 and therefore, the resulting coating solution cannot show the desired characteristic properties for the reasons discussed above. On the other hand, if the molar concentration of Si—$CH_3$ included in the blend of starting materials or a single starting material exceeds 130% of the molar concentration of Si included in the whole starting material, the value y of the resulting methylsiloxane oligomer likewise exceeds 1.3 and accordingly, any hardened film cannot be formed for the reasons discussed above.

Water is then added to the ingredient thus prepared in an amount of 2 to 4 times the molar amount of the latter and the condensation reaction thereof is initiated immediately after the addition of an organic carboxylic acid such as formic acid, acetic acid or succinic acid and thus a polymer is formed. If the amount of water is less than 2 times the molar amount of the ingredient, the reaction rate is considerably lowered and the rate of the alkoxy groups remaining in the polymer increases and correspondingly, this often leads to an increase in the amount of carbon remaining in the resulting film. On the other hand, if the amount of water exceeds 4 times the molar amount of the ingredient, not only the rate of production reaction is too high to control the reaction, but also the rate of free hydroxyl groups (Si—OH) in the methylsiloxane oligomer becomes too high and the resulting coating solution is insufficient in the storage stability.

The concentration of the organic carboxylic acid as a catalyst is not particularly restricted since it does not affect the structure and state of the product, but if the concentration thereof is extremely high, the reaction solution has a tendency to become acidic and this affects the stability of the resulting coating solution. Therefore, the concentration thereof should be as low as possible and preferably ranges from about 1/1000 to 1/100 mole on the basis of the ingredient. Inorganic acids such as hydrochloric acid and phosphoric acid other than organic acids should not be used since they have an influence on metals present on a substrate to which the coating solution is applied.

After the addition of water, the components of the liquid mixture is not generally compatible with one another and therefore, the mixture must vigorously be stirred using, for instance, a stirrer. Alcohols as by-products of the hydrolysis reaction are formed within several minutes to several hours and the hydrophilicity of the polymer formed increases. Accordingly, the components of the mixture are compatible with one another.

The reaction mixture may be diluted, in advance, by addition of a solvent such as alcohols prior to the polymerization reaction. For instance, the addition of methanol in an amount of 0.5 time the molar amount of the ingredient permits the reduction of heat generation at the initial stage of the reaction, improvement of the stability of the reaction through improvement in the compatibility of the components and retardation of the polymerization reaction. Solvents added to the reaction mixture for this purpose are, for instance, methanol, ethanol and dioxane and used in an amount ranging from 0.2 to 3 times the molar amount of the ingredient.

To polymerize the methylsiloxane oligomer till the weight-average molecular weight of the resulting polymer reaches 1500 to 6000, the foregoing reaction mixture is heated at a temperature of not less than 30° C. and not more than 80° C. In this respect, if the molar concentration of Si—$CH_3$ included in the blend of the starting materials or a single starting material relative to the molar concentration of Si present in the whole starting materials, i.e., the value y is relatively low, the polymerization is preferably carried out at a low temperature, while if the value y is relatively high, the oligomer is preferably polymerized at a relatively high temperature. If the heating temperature is less than 30° C., the polymerization rate is too low to obtain a polymer having a desired molecular weight. On the other hand, if the heating temperature exceeds 80° C., the control of the molecular weight of the resulting polymer becomes difficult since alcohols as by-products cause boiling and the polymerization reaction considerably rapidly proceeds. In general, it is preferred to carry out the reaction at a temperature of about 50° C. while maintaining the reaction system, in a sealed reactor, in a thermostatic chamber. The time required for the reaction varies depending on the reaction temperature used, but is not particularly limited and it is sufficient to properly select the reaction time so that it falls within the range of from about 4 to 120 hours while monitoring the molecular weight of the product formed.

Alcohols as by-products, a solvent when the solvent is added for dilution or the like, in addition to the water initially added as an ingredient coexist in the polymerization product thus obtained. They must be removed, but if the polymerization product is distilled or dried without any pretreatment, the concentration of the methylsiloxane oligomer is abruptly increased, the rate of polymerization acceleratedly rises and this leads to the formation of a gel having a molecular weight of not less than several hundreds of thousands. For this reason, the removal of the water, alcohols and solvent should be so designed that the concentration of the methylsiloxane oligomer is not increased. To this end, it is necessary to add, in advance, a main solvent used for the dilution, i.e., a solvent mainly comprising an organic compound having a boiling point of not less than 120° C. and not more than 200° C. to the polymerization product to dilute the product and to then distill the diluted product under ordinary pressure or a reduced pressure. In this respect, it is important to appropriately select the distillation temperature and pressure as conditions for the distillation so that the water, alcohols and solvent are distilled off, but the main solvent is not distilled off.

The same solvents used in the coating solution according to the third embodiment of the present invention can of course be used as such main solvents.

The methylsiloxane oligomer solution obtained after the removal of the water, alcohols and solvent according to the foregoing method may be used as such or may be subjected to addition of a proper solvent and optional filtration and ripening before practical use thereof as a coating solution.

The method for forming an insulating film for semiconductor devices according to the fifth embodiment of the present invention which makes use of the coating solution of the third embodiment of the present invention prepared according to the method of the fourth embodiment of the present invention and/or the coating solution of the second embodiment of the present invention comprises the steps of applying the coating solution according to the second and/or third embodiments of the present invention onto a distributing wire pattern formed on a silicon substrate and having step-like unevenness on the surface thereof, then drying the coated solution, maintaining the dried coating solution at a temperature of not less than 150° C. and not more than 300° C. for not less than 30 seconds to thus fluidize it and then hardening it at a temperature of not less than 350° C. and not more than 450° C. in a nitrogen gas atmosphere to form an insulating film. Thus, the present invention permits the production of a semiconductor device having an insulating film, in particular, an interlayer insulating film excellent in film characteristic properties.

This method is roughly identical to the conventional method for forming a film of an organic SOG, but the present invention is characterized in that the dried coating solution is maintained at a temperature of not less than 150° C. and not more than 300° C. for not less than 30 seconds, in the light of the fact that the SOG of the present invention has a self-fluidization temperature of not less than 150° C. and not more than 300° C., to thus complete the surface-leveling while making use of the self-fluidizing ability of the SOG. More specifically, a film obtained by applying the coating solution and then drying is again fluidized within the foregoing temperature range to thus ensure flatness of the surface over a wide area. The subsequent steps are no more than the usual ones called SOG curing steps.

EXAMPLES

The present invention will hereinafter be described in more specifically.

(Example 1)

A siloxane oligomer contained in a commercially available organic SOG was inspected for the rates of the foregoing structural units (a), (b), (c) and (d) present therein and the contents of organic substituents present therein. In this Example, two kinds of organic SOG's, i.e., Sample A (SF 1014 available from Sumitomo Chemical Co., Ltd.) and Sample B (Type 12000T available from Tokyo Ohka Kogyo Co., Ltd.) were analyzed.

Each organic SOG (Sample A or B; 1.5 ml each) and tris(acetylacetonato) Cr(III) (about 40 mg) were added to and dissolved in 1.5 ml of deutero acetone to give a uniform solution. The solution was introduced into an NMR sample tube of Teflon having an inner diameter of 10 mm and subjected to $^{29}$Si-NMR measurement using a Fourier transform NMR spectrometer (GX 270 available from JEOL Ltd.). The observed central frequency was 53.67 MHz, the observed frequency range was 16 kHz, the data points were 16 k or 32 k, the integration number was 10000–45000 and tetramethylsilane was used as the internal standard.

Figure 1:
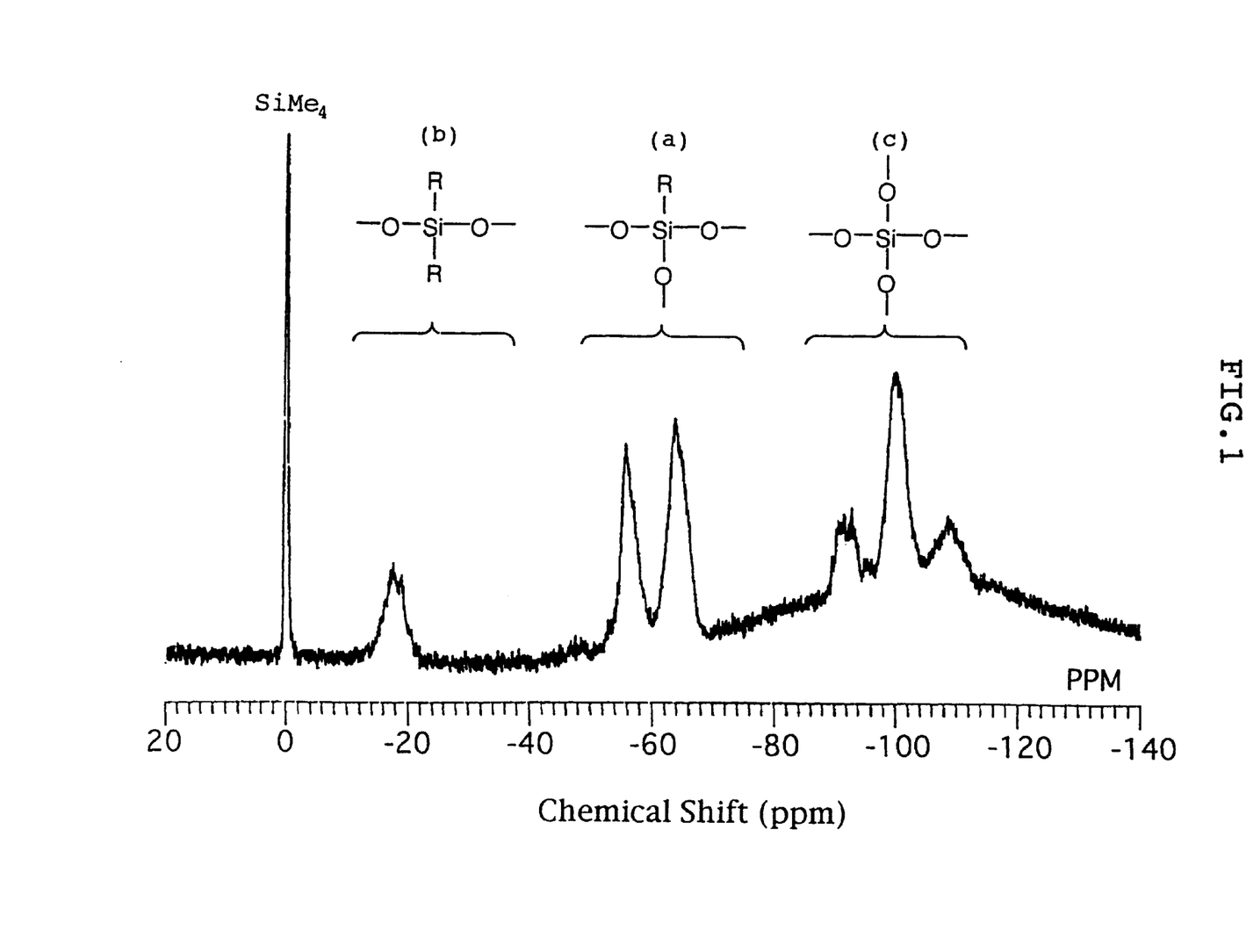
FIG. 1 is an $^{29}$Si-NMR spectrogram of the sample A (see Table 1) used in Example 1.

An example of the resulting $^{29}$Si-NMR spectrograms is shown in FIG. 1. The relative ratios of the foregoing $A_0$, $A_1$, $A_2$ and $A_3$ were determined on the basis of the area of each signal shown in FIG. 1. In this respect, the area of each peak shown in FIG. 1 is in proportion to the number of Si atoms present in each corresponding structural unit. In case of structural units (a) and (c), the sum of the areas of a plurality of peaks shown in FIG. 1 is in proportion to the number of Si atoms present in each structural unit.

In addition, the contents of the organic substituents defined by the foregoing Formula [3] were calculated. The results thus obtained are summarized in the following Table 1.

In this Example, the substituent R is a methyl group.

As has been described above, the rate of each structural unit (it has been impossible to determine the same by the conventional methods) present in organic siloxanes can be determined by analyzing the contents of organic substituents present in the organic siloxanes by the $^{29}$Si-NMR spectroscopic measurement using the evaluation method according to the first embodiment of the present invention. For instance, the evaluation method permits easy determination of the rates of the structural units (a), (b), (c) and (d) present in an organic SOG and the contents of organic substituents present therein.

TABLE 1

Rates of Structural Units and Contents of Organic Substituents

Rates of Structural Units
Rate (%) of the number of Si atoms present in each structural unit (a), (b), (c) or (d) to the total number of Si atoms present in siloxane

| | (d) $\begin{array}{c} R \\ | \\ R-Si-O- \\ | \\ R \end{array}$ | (b) $\begin{array}{c} R \\ | \\ -O-Si-O- \\ | \\ R \end{array}$ | (a) $\begin{array}{c} R \\ | \\ -O-Si-O- \\ | \\ O \\ | \end{array}$ | (c) $\begin{array}{c} | \\ O \\ | \\ -O-Si-O- \\ | \\ O \\ | \end{array}$ | Content of Organic Substituents Defined by Formula [3] |
|---|---|---|---|---|---|
| Sample A | 0 | 11 | 40 | 49 | 62 |
| Sample B | 0 | 0 | 46 | 54 | 46 |

(Example 2)

Methyltrimethoxysilane and tetramethoxysilane were dissolved in methanol in a rate listed in Table 2, followed by adding water in a rate listed in Table 1 and 0.002 mole of formic acid to the resulting solution and then carrying out a polymerization reaction at 30 to 60° C. for 24 hours with stirring. To the reaction product, there was added 650 ml of a 1:1 mixture of benzene and ethylene glycol monoethyl ether, followed by distillation under a reduced pressure to remove the excess methanol and water to give a coating solution having a solid content of about 20% by weight. The weight-average molecular weight of the siloxane oligomer included in the coating solution was determined by the gel permeation chromatography and was found to be about 3,000 which corresponded to a degree of polymerization ranging from 40 to 50.

The coating solution was applied onto a silicon wafer having a diameter of 6 inches by spin coating at a rotational frequency of 3,000 rpm, the resulting layer of the solution was baked at 150° C., 200° C. or 250° C. for 60 seconds and then heated at 400° C. for 30 minutes in a nitrogen gas stream to give a coating film.

The resulting film was inspected for the shrinkage factor, dielectric constant and water absorption. The results thus obtained are shown in the following Table 2 and FIG. 2 together with the value X defined by Formula [2].

In this respect, the shrinkage factor was evaluated by forming coating films different, in thickness, from one another on washed semiconductor substrates while controlling the rotational frequency and then calculating the factor according to the following Formula [5]:

$$\text{Shrinkage Factor (\%)} = \{(t_b - t_a)/t_b\} \times 100 \qquad [5]$$

wherein $t_a$ represents the thickness of the film after the hardening treatment and $t_b$ represents the thickness of the film after the prebaking treatment.

The dielectric constant was determined by forming an Al film on the whole surface of a washed semiconductor substrate through sputtering, then forming a coating film having a thickness of about 300 nm while controlling the rotational frequency according to the foregoing method, subjecting the film to prebaking and curing treatments, vapor-depositing an Al electrode of about 3 mm square through a metal mask, etching the edge portion of the film with diluted hydrofluoric acid, measuring the electrostatic capacity between the lower whole Al surface and the vapor-deposited Al film and calculating the dielectric constant on the basis of the electrode surface area and the film thickness.

Moreover, the water absorption, i.e., the amount of water included in the film was determined by allowing, to stand, a film after the completion of the hardening treatment for 24 hours in a clean room and then measuring the amount of water generated till the temperature reached 400° C. using an electrolytic cell type moisture meter (MEA (Moisture Evaluation Analyzer) available from duPont de Nemours & Co.).

Figure 2:
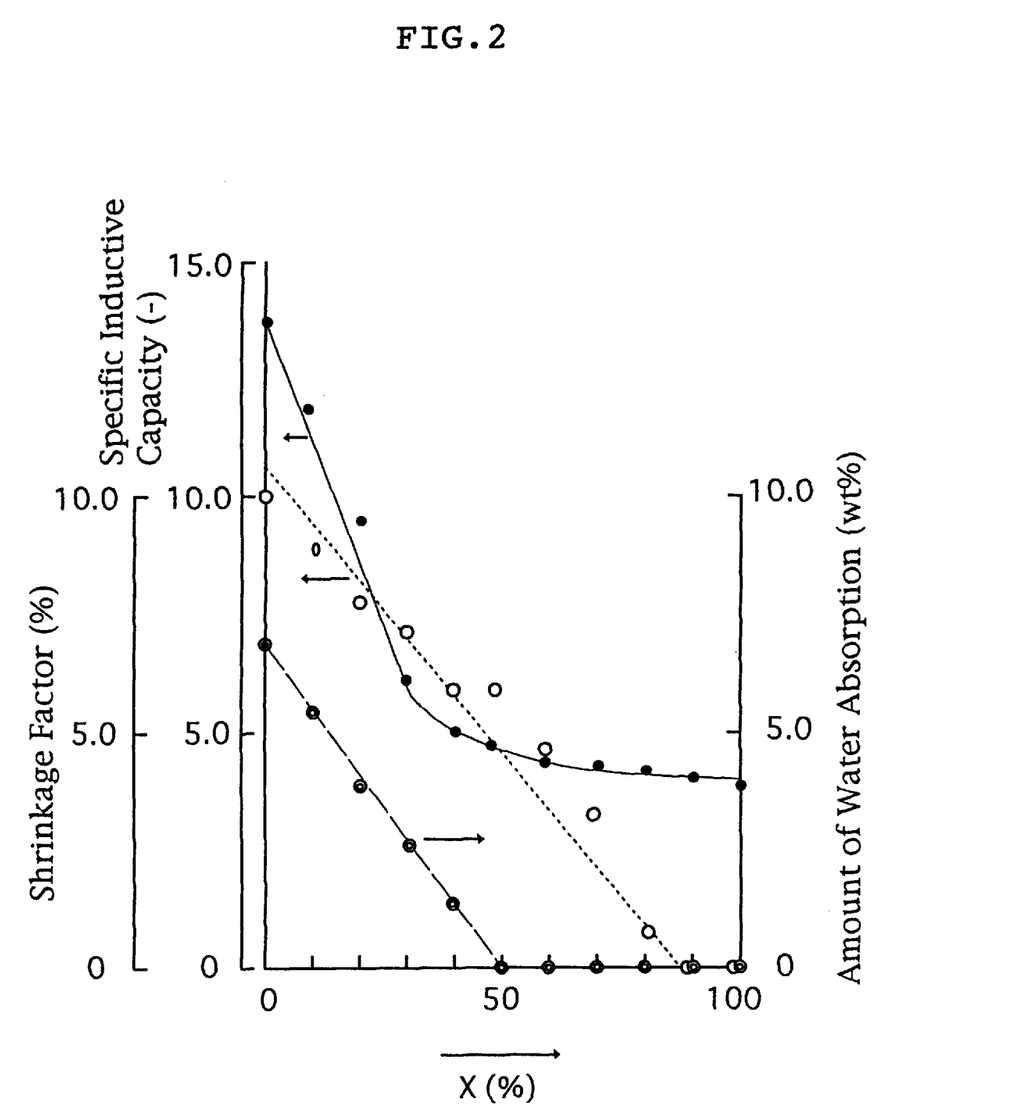
FIG. 2 is a graph showing the relation between the value X defined by Formula [2] in Example 2 and the shrinkage factor, the relative dielectric constant or the water absorption of an insulating film.

As seen from Table 2 and FIG. 2, there is a distinct relation between the value X and the film properties and it has also been found that when X≧80%, an excellent film can be obtained, whose shrinkage factor, dielectric constant and water absorption are low.

TABLE 2

| No. | Methyltrimethoxy-silane (mole) | Tetramethoxy-silane (mole) | Water (mole) | Reaction Temperature (° C.) | X Defined by Formula [2] | Shrinkage Factor (%) | Specific Inductive Capacity (−) | Absorption (wt %) | Remarks |
|---|---|---|---|---|---|---|---|---|---|
| 1 | 0.0 | 1.0 | 0.5 | 30 | 0 | 10.0 | 14.0 | 6.6 | Comparative |
| 2 | 0.1 | 0.9 | 0.5 | 30 | 10 | 9.0 | 12.0 | 5.0 | Examples |
| 3 | 0.2 | 0.8 | 1.0 | 30 | 20 | 8.0 | 9.5 | 3.9 | |
| 4 | 0.3 | 0.7 | 1.0 | 30 | 30 | 7.2 | 6.2 | 2.9 | |

TABLE 2-continued

| No. | Methyltrimethoxy-silane (mole) | Tetramethoxy-silane (mole) | Water (mole) | Reaction Temperature (° C.) | X Defined by Formula [2] | Shrinkage Factor (%) | Specific Inductive Capacity (−) | Absorption (wt %) | Remarks |
|---|---|---|---|---|---|---|---|---|---|
| 5 | 0.4 | 0.6 | 1.5 | 50 | 40 | 6.0 | 5.3 | 1.6 | |
| 6 | 0.5 | 0.5 | 2.0 | 50 | 50 | 5.8 | 4.4 | 0.2 | |
| 7 | 0.6 | 0.4 | 2.0 | 50 | 60 | 4.3 | 4.1 | 0.1 | |
| 8 | 0.7 | 0.3 | 2.0 | 50 | 70 | 3.2 | 3.8 | 0.0 | |
| 9 | 0.8 | 0.2 | 2.0 | 80 | 80 | 0.8 | 3.5 | 0.0 | Present |
| 10 | 0.9 | 0.1 | 2.0 | 80 | 90 | 0.0 | 3.2 | 0.0 | Invention |
| 11 | 1.0 | 0.0 | 2.0 | 80 | 100 | 0.0 | 3.0 | 0.0 | |

(Example 3)

First of all, a coating solution of the present invention for forming SOG films was prepared according to the following procedures according to the method of the fourth embodiment of the present invention. In the preparation, the mixing ratios of starting materials, the conditions for synthesis and the typical film properties are summarized in the following Tables 3 and 4. Table 3 shows three kinds of starting materials which are variously combined, while Table 4 shows data obtained when a variety of conditions for synthesis are variously changed. Data practically determined are also listed in Tables 3 and 4. The details of the methods for determination will be described below. Physical properties of the film determined in this Example are the same as those listed in Tables 3 and 4. The films beyond the scope of the present invention are comparative examples and specified by annexing an asterisk (*) to the front of each corresponding sample number.

(Synthesis of Coating Solution)

Tetramethoxysilane, methyltrimethoxysilane and dimethyldimethoxysilane (the purity of these compounds being not less than 99%) were admixed together in mixing ratios specified in Table 3 and 4, followed by adding water to each mixture in a rate listed in Table 3 or 4, further adding a 1N formic acid aqueous solution in an amount of 0.002 mole as expressed in terms of formic acid, stirring the mixture to give a uniform solution, closely sealing the container including the mixture, immersing the container in a thermostatic water bath maintained at a temperature specificed in Table 3 or 4 and polymerizing the mixture by maintaining it at that temperature for a time listed in Table 3 or 4. Methyl n-amyl ketone (2-heptanone; boiling point: 151° C.) was added to the polymerized product as a solvent, followed by distilling the mixture at 50° C. and 50 Torr using a rotary evaporator to remove the excess methanol and water. Thereafter, the mixture was further diluted with methyl n-amyl ketone (2-heptanone) to give a coating solution having a solid content of 20% by weight. The weight-average molecular weight of the siloxane oligomer included in the coating solution was determined by the gel permeation chromatography and the results were also listed in Table 4. It is clear that all of the coating solutions synthesized in Examples shown in Table 4 satisfy the requirements for the coating solution according to the third embodiment of the present invention, except for the irregularity of the Si—O—Si network since there has not been developed any method capable of determining the irregularity. However, it is self-evident that the siloxane oligomers do not have a regular structure such as a ladder structure while taking into consideration the fact that the shrinkage factor as will be detailed below is very small.

Each coating solution was applied onto a silicon wafer having a diameter of 6 inches by spin coating at a rotational frequency of 3,000 rpm, the resulting layer of the solution was baked at 150° C., 200° C. or 250° C. for 60 seconds and then heated at 400° C. for 30 minutes in a nitrogen gas stream to give a coated film.

The resulting film was inspected for the shrinkage factor, dielectric constant and water absorption. The results thus obtained are shown in the following Table 3 together with the value y in the following chemical formula 1:

$(CH_3)_y\ SiO_{2(y/2)}$ (chemical formula 1)

The shrinkage factor, dielectric constant and water absorption of the film were determined and evaluated in the same manner used in Example 2.

As seen from Tables 3 and 4, there is a distinct relation between the value y and the film properties and it has also been found that when $0.8 \leq y \leq 1.3$, an excellent film can be obtained, whose shrinkage factor and dielectric constant are small and whose water content is low.

Then the method for forming an insulating film according to the fifth embodiment of the present invention will be explained below with reference to the attached drawings.

Figure 3:
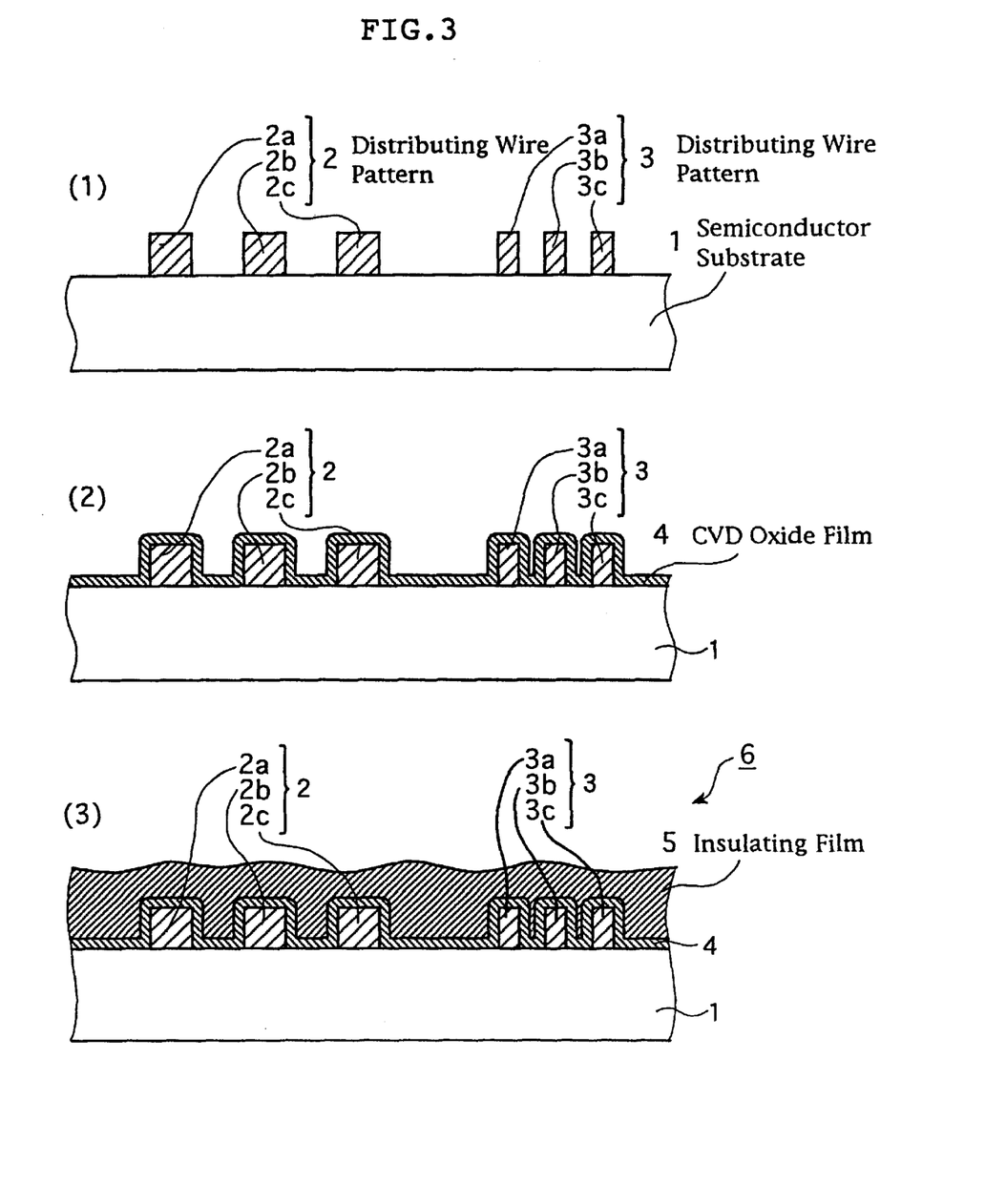
FIGS. 3(A), 3(B) and 3(C) are schematic partially sectional views showing a process for forming a distributing wire pattern, a CVD oxide film-forming process and a process for forming an insulating film in the method for producing an insulating film for semiconductor devices according to the present invention, respectively.

FIG. 3 is a partially sectional view showing the processes for forming an insulating film according to the present invention. In the process shown in FIG. 3(A), a distributing wire layer having a thickness of 1.2 μm was formed on a semiconductor substrate 1 which has been subjected to a desired treatment, then the layer was subjected to patterning to form a line-and-space distributing wire pattern 2 comprising distributing wires 2a, 2b and 2c having a width of the wire of 1 μm (distance between the wires 2a and 2b=distance between the wires 2b and 2c=1 μm) and a line-and-space distributing wire pattern 3 comprising distributing wires 3a, 3b and 3c having a width of the wire of 0.5 μm (distance between the wires 2a and 2b=distance between the wires 2b and 2c=0.5 μm). The distance between the distributing wire patterns 2 and 3 was set at 3 μm. This process was accompanied by the formation of steps between the semiconductor substrate 1 and the distributing wire patterns 2 and 3.

In the subsequent process shown in FIG. 3(B), an $SiO_2$ layer 4 was deposited on the whole surface of the semiconductor substrate 1 and the distributing wire patterns 2 and 3 obtained in the process shown in FIG. 3 (A) in a thickness of 300 nm by the plasma CVD technique using tetraethoxysilane (TEOS). This CVD oxide film 4 is excellent in the step coverage, but could not fill up the grooves between the distributing wires since the film was formed along the shape (steps) of the surface of the substrate.

Figure 4:
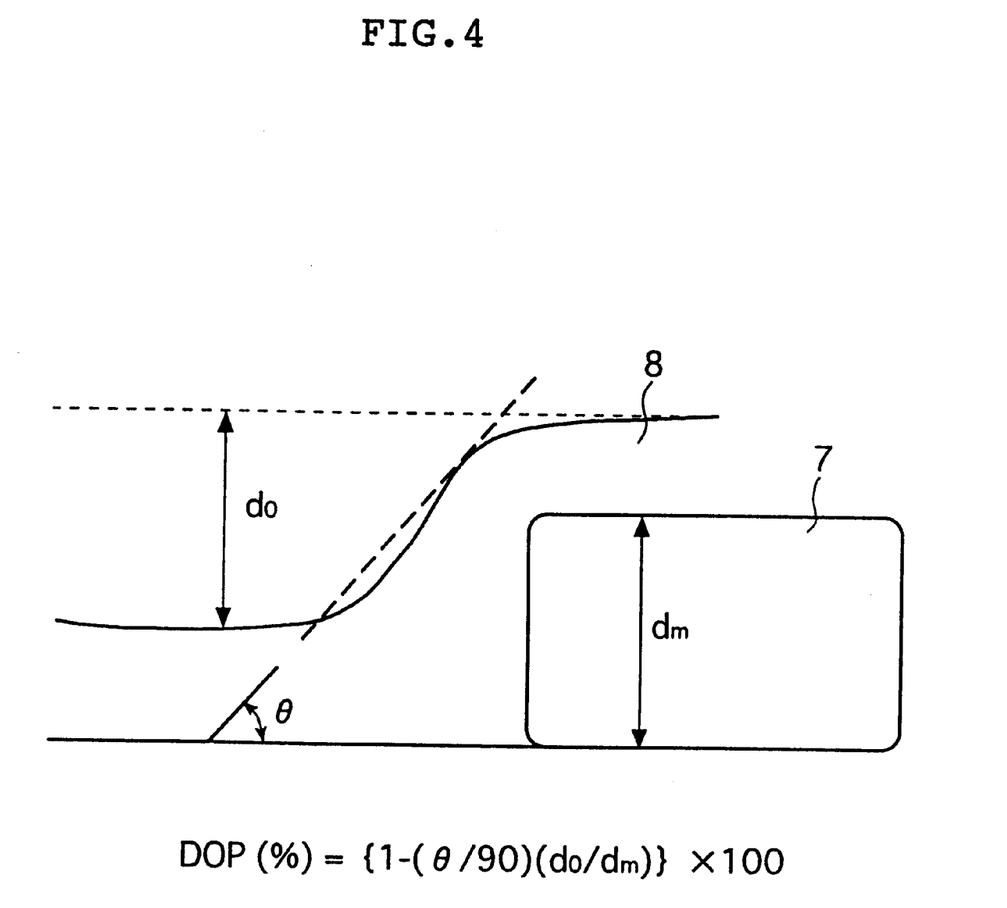
FIG. 4 is a schematic cross sectional view showing a step formed on an insulating film, for explaining the method for determining DOP as a measure for the flatness as determined in Example 3.

In the next process shown in FIG. 3(C), each coating solution prepared in the foregoing method and shown in Table 3 or 4 as an ingredient for an insulating film was applied onto the oxide film 4 in a thickness ranging from 0.7 or 1.1 μm by the spin coating technique to form an insulating film 5 and the resulting layer of the solution was pre-baked at 80° C., 150° C. or 230° C. for 60 seconds in a nitrogen gas atmosphere. Thereafter, the pre-baked layer was cured (hardened) by heating it at 400° C. for 30 minutes in a nitrogen gas stream to give an insulating film 5. Thus, a semiconductor device 6 of the present invention was produced. The cross section of the insulating film S of the resulting semiconductor device 6 was observed. In the evaluation of the flatness, the tendency of the insulating film was specifically examined using the measure (DOP) for the flatness shown in FIG. 4. Incidentally, the measure for the flatness, i.e., DOP (%) was determined according to the following equation:

$$\text{DOP (\%)} = \{[1-(\theta/90)(d_0/d_m)]\} \times 100$$

wherein θ represents the slope of the step of the insulating film 8 originated from the distributing wire 7 as shown in FIG. 2; $d_0$ represents the difference of altitude; and $d_m$ represents the thickness of the distributing wire 7.

The results of the measurement of the flatness are listed in Tables 3 and 4.

It is found that excellent flatness can be ensured through the use of either of the SOG's according to the present invention.

TABLE 3

| Ex. No. | Tetramethoxy-silane (mole) | Methyltri-methoxy-silane (mole) | Dimethyl-dimethoxy-silane (mole) | Water (mole) | Reaction Condition | Value y in Chemical Formula 1 | Shrinkage Factor (%) | Dielectric Constant | Flatness DOP (%) | Water Absorption (wt %) | Remarks |
|---|---|---|---|---|---|---|---|---|---|---|---|
| *1 | 1.0 | 0.0 | 0.0 | 3 | 50° C., 24 h | 0.0 | 25 | 5.4 | 0.50 | 6.6 | formation of cracks |
| 2 | 0.3 | 0.7 | 0.0 | 3 | 50° C., 24 h | 0.7 | 6 | 4.2 | 0.65 | 1.8 | |
| 3 | 0.2 | 0.8 | 0.0 | 3 | 50° C., 24 h | 0.8 | 3 | 3.5 | 0.90 | 0.2 | |
| 4 | 0.1 | 0.9 | 0.0 | 3 | 50° C., 24 h | 0.9 | 1 | 3.3 | 0.90 | <0.1 | |
| 5 | 0.0 | 1.0 | 0.0 | 3 | 50° C., 24 h | 1.0 | 0 | 3.0 | >0.90 | <0.1 | |
| 6 | 0.1 | 0.8 | 0.1 | 3 | 50° C., 24 h | 1.0 | 0 | 3.0 | >0.90 | <0.1 | |
| 7 | 0.5 | 0.0 | 0.5 | 3 | 50° C., 24 h | 1.0 | 0 | 3.0 | >0.90 | <0.1 | |
| 8 | 0.0 | 0.9 | 0.1 | 3 | 50° C., 24 h | 1.1 | 0 | 2.9 | >0.90 | <0.1 | |
| 9 | 0.1 | 0.7 | 0.2 | 3 | 50° C., 24 h | 1.1 | 0 | 2.9 | >0.90 | <0.1 | |
| 10 | 0.0 | 0.8 | 0.2 | 3 | 50° C., 24 h | 1.2 | 0 | 2.9 | >0.90 | <0.1 | |
| 11 | 0.0 | 0.74 | 0.28 | 3 | 50° C., 24 h | 1.3 | 0 | 2.8 | >0.90 | <0.1 | |
| 12 | 0.2 | 0.3 | 0.5 | 3 | 50° C., 24 h | 1.3 | 0 | 2.7 | >0.90 | <0.1 | |
| *13 | 0.0 | 0.6 | 0.4 | 3 | 50° C., 24 h | 1.4 | — | — | — | — | film is not formed |
| *14 | 0.3 | 0.0 | 0.7 | 3 | 50° C., 24 h | 1.4 | — | — | — | — | film is not formed |

TABLE 4

| Ex. No. | Tetramethoxy-silane (mole) | Methyltri-methoxy-silane (mole) | Dimethyl-dimethoxy-silane (mole) | Water (mole) | Reaction Condition | Averaged molecular weight of Oligomer | Shrinkage Factor (%) | Dielectric Constant | Flatness DOP (%) | Water Absorption (wt %) | Remarks |
|---|---|---|---|---|---|---|---|---|---|---|---|
| *15 | 0.0 | 1.0 | 0.0 | 1 | 50° C., 24 h | 1200 | 7 | 3.3 | 0.70 | <0.1 | uneven in film thickness |
| 16 | 0.0 | 1.0 | 0.0 | 2 | 50° C., 24 h | 1900 | 1 | 3.1 | >0.90 | <0.1 | |
| 17 | 0.0 | 1.0 | 0.0 | 3 | 50° C., 24 h | 2500 | 0 | 2.9 | >0.90 | <0.1 | |
| 18 | 0.0 | 1.0 | 0.0 | 4 | 50° C., 24 h | 2800 | 0 | 2.9 | >0.90 | <0.1 | |
| *19 | 0.0 | 1.0 | 0.0 | 5 | 50° C., 24 h | 9000 | 0 | 2.9 | >0.90 | <0.1 | uneven in film thickness |
| *20 | 0.0 | 1.0 | 0.0 | 3 | 30° C., 24 h | 700 | 10 | 3.6 | 0.70 | <0.1 | uneven in film thickness |
| 21 | 0.0 | 1.0 | 0.0 | 3 | 40° C., 24 h | 1600 | 0 | 3.0 | >0.90 | <0.1 | |
| 22 | 0.0 | 1.0 | 0.0 | 3 | 60° C., 24 h | 2800 | 0 | 3.0 | >0.90 | <0.1 | |
| 23 | 0.0 | 1.0 | 0.0 | 3 | 70° C., 24 h | 5200 | 0 | 3.0 | >0.90 | <0.1 | |
| 24 | 0.0 | 1.0 | 0.0 | 3 | 60° C., 24 h | 4000 | 0 | 3.0 | >0.90 | <0.1 | |

INDUSTRIAL APPLICABILITY

As has been described above in detail, the evaluation method according to the present invention permits, in the analysis of the contents of organic substituents of organic siloxanes, the determination of the rate of each structural unit (it has been impossible to determine the same by the conventional methods) present in the organic siloxanes and the determination of the contents of the organic substituents present in the organic siloxanes.

Therefore, the present invention can be used for evaluating the organicity of the siloxanes present in a solution containing the same which is used for forming, for instance, an insulating film for semiconductor devices, in particular, an interlayer insulating film for LSI multilevel interconnections and the evaluation method of the present invention permits the prediction of the film properties of the insulating film such as the resistance to chemicals and the water resistance. Moreover, the present invention has such an effect that the accurate quality control of SOG's used for forming an insulating film can be ensured during the production of the SOG's.

In addition, the use of the coating solution containing the siloxanes of the present invention, in particular, methylsiloxane oligomer permits the formation of an insulating film for semiconductor devices such as an interlayer insulating film for LSI multilevel interconnections having excellent film properties.

In other words, if using the coating solution and the method for forming an insulating film, which makes use of the coating solution, according to the present invention, an insulating film having excellent film properties can be prepared, i.e., they permit the achievement of uniform flatness over the whole pattern on the substrate and complete filling up of fine grooves, the resulting insulating film exhibits excellent resistance to cracks, they can form a thick film sufficient for eliminating the steps on the substrate, i.e., leveling the substrate surface and they permit the formation of an insulating film free of moisture, having a low dielectric constant and effective for use in high speed interconnections, in particular, an interlayer insulating film for semiconductor devices.

In addition, the method for preparing the coating solution of the present invention permits stable production of a coating solution showing the foregoing effects with certainty.

Furthermore, the method for producing a semiconductor device according to the present invention likewise permits stable production of semiconductor devices provided with interlayer insulating films excellent in the foregoing film properties, with certainty.

What is claimed is:

1. A coating solution for forming an insulating film over a surface of a substrate, the coating solution comprising a solvent and siloxanes dissolved in the solvent, the siloxanes represented by a general formula:

where each of k, l, m and n is an integer ranging from 0 to 1000, at least one of k, l and m is greater than zero, R may be the same or different and represents at least one organic group selected from the group consisting of a saturated hydrocarbon group, an unsaturated hydrocarbon group, a phenyl group and a substituted phenyl group, and a ratio of (3k+2l+m) to (k+l+m+n) is not less than about 0.8 and not more than 1.3, wherein the coating solution, when coated over the surface, is self-fluidizable at a temperature of not less than 150° C. and not more than 300° C.

2. The coating solution according to claim 1, wherein the siloxanes are random structured siloxanes.

3. The coating solution according to claim 1, wherein R of the siloxanes represents an alkyl group.

4. The coating solution according to claim 1, wherein R of the siloxanes represents a methyl group.

5. The coating solution according to claim 1, wherein the coating solution is self-fluidizable at a temperature ranging from 150° to 200° C.

6. The coating solution according to claim 1, wherein k is substantially equal to zero.

7. The coating solution according to claim 1, wherein a ratio of m to (k+l+m+n) is less than one.

8. The coating solution according to claim 1, wherein the solvent of the coating solution includes an organic compound having a boiling point of not less than 120° C. and not more than 200° C.

9. The coating solution according to claim 8, wherein the boiling point of the organic compound ranges from 130° C. to 160° C.

10. The coating solution according to claim 1, wherein a weight average molecular weight of the siloxanes in the coating solution is between 1500 and 6000.

11. The coating solution according to claim 3, wherein k is substantially equal to zero.

12. The coating solution according to claim 3, wherein a ratio of m to (k+l+m+n) is less than one.

13. The coating solution according to claim 3, wherein the coating solution is self-fluidizable at a temperature ranging from 150° C. to 200° C.

14. The coating solution according to claim 4, wherein k is substantially equal to zero.

15. The coating solution according to claim 4, wherein a ratio of m to (k+l+m+n) is less than one.

16. The coating solution according to claim 4, wherein the coating solution is self-fluidizable at a temperature ranging from 150° to 200° C.

17. The coating solution according to claim 4, wherein the solvent of the coating solution includes an organic compound having a boiling point of not less than 120° C. and not more than 200° C.

18. The coating solution according to claim 17, wherein the boiling point of the organic compound ranges from 130° C. to 160° C.

* * * * *